US012733867B2

(12) United States Patent
Patwardhan

(10) Patent No.: US 12,733,867 B2
(45) Date of Patent: Sep. 15, 2026

(54) ACNE SEVERITY GRADING METHODS AND APPARATUSES

(71) Applicant: Canfield Scientific, Incorporated, Parsippany, NJ (US)

(72) Inventor: Sachin V. Patwardhan, Mount Tabor, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 461 days.

(21) Appl. No.: 18/029,902

(22) PCT Filed: Oct. 19, 2021

(86) PCT No.: PCT/US2021/055577
§ 371 (c)(1),
(2) Date: Apr. 1, 2023

(87) PCT Pub. No.: WO2022/086938
PCT Pub. Date: Apr. 28, 2022

(65) Prior Publication Data

US 2023/0363697 A1 Nov. 16, 2023

Related U.S. Application Data

(60) Provisional application No. 63/093,801, filed on Oct. 20, 2020.

(51) Int. Cl.
*A61B 5/00* (2006.01)

(52) U.S. Cl.
CPC ............ *A61B 5/445* (2013.01); *A61B 5/0071* (2013.01); *A61B 5/0077* (2013.01)

(58) Field of Classification Search
CPC ...... A61B 5/445; A61B 5/0071; A61B 5/0077
(Continued)

(56) References Cited

U.S. PATENT DOCUMENTS 7,006,223 B2 * 2/2006 Mullani ................. A61B 5/445 356/369
8,498,460 B2 7/2013 Patwardhan
(Continued)

FOREIGN PATENT DOCUMENTS

EP 1693003 A1 * 8/2006 ............ A61B 5/442

OTHER PUBLICATIONS

Xu, D. T., Yan, J. N., Cui, Y., & Liu, W. (2016). Quantifying facial skin erythema more precisely by analyzing color channels of The VISIA Red images. Journal of Cosmetic and Laser Therapy, 18(5), 296-300. https://doi.org/10.3109/14764172.2016.1157360 (Year : 2016).*

(Continued)

*Primary Examiner* — Jennifer Mehmood
*Assistant Examiner* — Eric James Shoemaker

(57) ABSTRACT

Apparatuses and methods are disclosed for generating scores indicative of the severity of an acne condition of skin based on images of the skin. In exemplary implementations, a cross-polarized image with a skin area appearing therein is obtained and transformed to generate a red component image which is used to detect erythema in the skin area. A texture image with the skin area appearing therein is also obtained and is used to detect raised portions of the skin area. An acne severity score based on the erythema and raised portions detected in the skin area is generated and an indication thereof is output. Additionally, a fluorescence image with the skin area appearing therein can also be obtained and used to detect portions of the skin area containing a porphyrin indicative of acne, which can also be used in generating the acne severity score.

21 Claims, 6 Drawing Sheets

(58) Field of Classification Search
USPC .......................................................... 382/128
See application file for complete search history.

(56) References Cited

U.S. PATENT DOCUMENTS

| | | | |
|---|---|---|---|
| 8,849,380 | B2 | 9/2014 | Patwardhan |
| 10,368,795 | B2 | 8/2019 | Patwardhan |
| RE47,921 | E | 3/2020 | Patwardhan |
| 10,702,160 | B2 | 7/2020 | Patwardhan |
| 2019/0336003 | A1 | 11/2019 | Patwardhan |

OTHER PUBLICATIONS

P.R. Bargo, N. Kollias, Measurement of skin texture through polarization imaging, British Journal of Dermatology, vol. 162, Issue 4, Apr. 1, 2010, pp. 724-731, https://doi.org/10.1111/j.1365-2133.2010.09639.x (Year: 2010).*

Stamatas, G.N., Kollias, N. (2014). Modern Technology for Imaging and Evaluation of Acne Lesions. In: Zouboulis, C., Katsambas, A., Kligman, A. (eds) Pathogenesis and Treatment of Acne and Rosacea. Springer, Berlin, Heidelberg. https://doi.org/10.1007/978-3-540-69375-8_45 (Year: 2014).*

Youngwoo Bae, J. Stuart Nelson M.D., Byungjo Jung. Multimodal facial color imaging modality for objective analysis of skin lesions. Nov. 2008. Journal of Biomedical Optics, vol. 13, Issue 6, 064007 (Nov. 2008). https://doi.org/10.1117/1.3006056 (Year: 2008).*

Tan JK, Tang J, Fung K, Gupta AK, Thomas DR, Sapra S, Lynde C, Poulin Y, Gulliver W, Sebaldt RJ. Development and validation of a comprehensive acne severity scale. J Cutan Med Surg. Nov.-Dec. 2007;11(6):211-6. doi: 10.2310/7750.2007.00037. PMID: 18042334. (Year: 2007).*

I. Seo, S. H. Tseng, G. O. Cula, et al. "Fluorescence spectroscopy for endogenous porphyrins in human facial skin", Proc. SPIE 7161, Photonic Therapeutics and Diagnostics V, 716103 (Feb. 19, 2009); https://doi.org/10.1117/12.811913 (Year: 2009).*

J.K.L. Tan et al., Reliability of Dermatologists in Acne Lesion Counts and Global Assessments, J. Cutan. Med. Surg., Jul.-Aug. 2006;10(4):160-5, DOI: 10.2310/7750.2006.00044.

H.M. Singer et al., Using Network Oriented Research Assistant (NORA) Technology to Compare Digital Photographic with In-Person Assessment of Acne Vulgaris, JAMA Dermatol. 2018;154(2):188-190, DOI:10.1001/iamadermatol.2017.5141.

Z.V. Lim et. al., Automated Grading of Acne Vulgaris by Deep Learning with Convolutional Neural Networks, Skin Research and Technology, vol. 26/2, Mar. 2020, pp. 187-192.

S.V. Patwardhan et al., Measuring acne using Coproporphyrin III, Protoporphyrin IX, and lesion-specific inflammation: an exploratory study, Arch. of Derm. Res., Apr; 309(3):159-167, 2017, DOI: 10.1007/s00403-017-1718-3.

I. Kohli et al., Quantitative measurement of skin surface oiliness and shine using differential polarized images, Arch. of Derm. Res., 2020. DOI: 10.1007/s00403-020-02070-5.

G. Dobos et al., Effects of intrinsic aging and photodamage on skin dyspigmentation: an explorative study, J. Biomed Opt., Jun. 1, 2016;21(6):66016. DOI: 10.1117/1.JBO.21.6.066016. PMID: 27330007.

Extended European Search Report, EP Application No. 21883682.3, Sep. 20, 2024.

Patwardhan, Sachin V, et al., Auto-Classification of Acne Lesions Using Multimodal Imaging, Journal of Drugs In Dermatology, Strategic Communication in Dermatology, New York, NY, vol. 12, No. 7, Jul. 1, 2013, pp. 746-756.

Choi et al., Cosmetic efficacy evaluation of an anti-acne cream using the 3D image analysis system, Skin Research and Technology 2012; 18: 192-198.

* cited by examiner

*FIG. 4A*
*FIG. 4B*
IGA -2
Subject 22
IGA -3
Subject 24
IGA -4
Subject 23
IGA -5
Subject 15
IGA-2
IGA-3
IGA-4
IGA-5

ACNE SEVERITY GRADING METHODS AND APPARATUSES

RELATED APPLICATIONS

This Application is a U.S. National Phase filing of International Patent Application No. PCT/US2021/055577 filed 19 Oct. 2021, which claims priority from U.S. Provisional Patent Application No. 63/093,801 filed Oct. 20, 2020. Each of the aforementioned applications is hereby incorporated herein by reference in its entirety.

BACKGROUND INFORMATION

The present disclosure relates to image processing and analysis, particularly the grading of the severity of acne in human skin based on images thereof.

Acne is one of the most common skin conditions affecting millions of people worldwide. There are considerable negative effects of acne including lifelong scarring, feelings of low self-esteem, and an impaired quality of life.

Acne often requires treatment with combinations of drugs, many of which are expensive. Large sums of money are spent annually on the treatment of acne, both for office visits and for over-the-counter and prescription drugs, with little or no ability to estimate their benefits. In this era of ever-changing paradigms in health care delivery, it is essential that health care providers base treatment decisions on data generated through evidence-based analyses.

The lack of standardization in how acne is assessed in clinical trials makes it difficult to pool data from different trials of the same treatment and impossible for clinicians to know the relative effectiveness of different types of treatment. Health care providers need this information to guide their treatment recommendations for patients with acne.

The primary end points of a typical acne clinical study are the lesion counts and the Investigator's Global Assessment (IGA) grade of acne severity. The Food and Drug Administration recommends that the study sponsors discuss their IGA scales and study designs with them before trial implementation. Neither the lesion counting or grading approaches, however, have been standardized, and maintaining consistency within and across studies is challenging due to the evaluators' subjectivity. Most IGA scales use terms such as "none", "few", "several", "moderate" or "many" inflammatory/non-inflammatory lesions as severity grade descriptors. Some scales also look at the lesion distribution using area of involvement descriptions, such as "less than half", "more than half", or "entire area." Furthermore, a study has reported that dermatologists tend to be less reliable in making global assessments than in counting acne lesions, and that reliability depends on training. (J. K. L. Tan et al. Reliability of Dermatologists in Acne Lesion Counts and Global Assessments, J. Cutan. Med. Surg., Jul-Aug 2006; 10(4):160-5, doi: 10.2310/7750.2006.00044.)

In the meantime, the importance of image-based skin evaluation has increased with the exponential growth of teledermatology in the past several decades. A study with 69 subjects has reported agreement between acne evaluations performed in-person and from selfie images captured by the subject. (H. M. Singer et al. Using Network Oriented Research Assistant (NORA) Technology to Compare Digital Photographic with In-Person Assessment of Acne Vulgaris, JAMA Dermatol. 2018:154(2):188-190. doi:10.1001/jamadermatol.2017.5141.) A deep-learning algorithm using frontal photographs of 416 acne patients trained to generate automated IGA scores has been reported to give the best classification accuracy of 67% with a Pearson correlation of 0.77 between machine-predicted score and the clinical scoring for various image input sizes. (Z. V. Lim et. al. Automated Grading of Acne Vulgaris by Deep Learning with Convolutional Neural Networks, Skin Research and Technology. Volume 26/2. March 2020, Pages 187-192.)

One effort to improve how acne and its impacts are measured is the Acne Core Outcomes Research Network (ACORN), which was formed with the goal of developing a "toolbox" of validated methods to assess acne that can be adopted by researchers conducting clinical trials worldwide. It is hoped that the use of such standardized outcome measures would generate valuable information to help guide treatment recommendations.

In any case, there is still a need for image-based, acne evaluation systems and methodologies that can reliably, reproducibly, and objectively grade acne, which can replace or supplement the IGA grading done currently. There is a further desire that the grading generated by such systems and methodologies be comparable to those of the IGA currently in use, to thereby allow meaningful comparisons therebetween.

SUMMARY OF THE DISCLOSURE

As described herein, the relationships between individual acne related visible features and Investigator Global Assessment (IGA) grading of acne severity were evaluated. Acne-related inflammation or erythema, raised-lesion topography, microbial fluorescence, and skin surface oiliness were measured from multi-modal images of the subjects and their relationships with the IGA grading were individually evaluated. The relationship between inflammatory and non-inflammatory lesion counts and IGA was also evaluated. Based on this analysis, methods and apparatuses are disclosed employing multi-factorial measurement combinations as objective and repetitive alternatives to IGA for the global assessment of acne severity.

In exemplary implementations, the present disclosure sets out a method comprising: obtaining a cross-polarized image with a skin area appearing therein; transforming the cross-polarized image to generate a red component image; detecting erythema in the skin area using the red component image; obtaining a texture image with the skin area appearing therein; detecting raised portions of the skin area using the texture image; generating an acne severity score based on the erythema and raised portions detected in the skin area; and outputting an indication of the acne severity score.

The present disclosure also sets out, in exemplary implementations, an apparatus comprising: a storage device configured to store instructions; and a processor configured to execute instructions stored in the storage device to: obtain a cross-polarized image with a skin area appearing therein; transform the cross-polarized image to generate a red component image; detect erythema in the skin area using the red component image; obtain a texture image with the skin area appearing therein; detect raised portions of the skin area using the texture image; generate an acne severity score based on the erythema and raised portions detected in the skin area; and output an indication of the acne severity score.

These and other aspects of such apparatuses and methods and exemplary variants thereof are described in greater detail below.

BRIEF DESCRIPTION OF THE DRAWINGS

A more complete understanding of the present disclosure may be realized by reference to the accompanying drawings.

DETAILED DESCRIPTION

Figure 1:
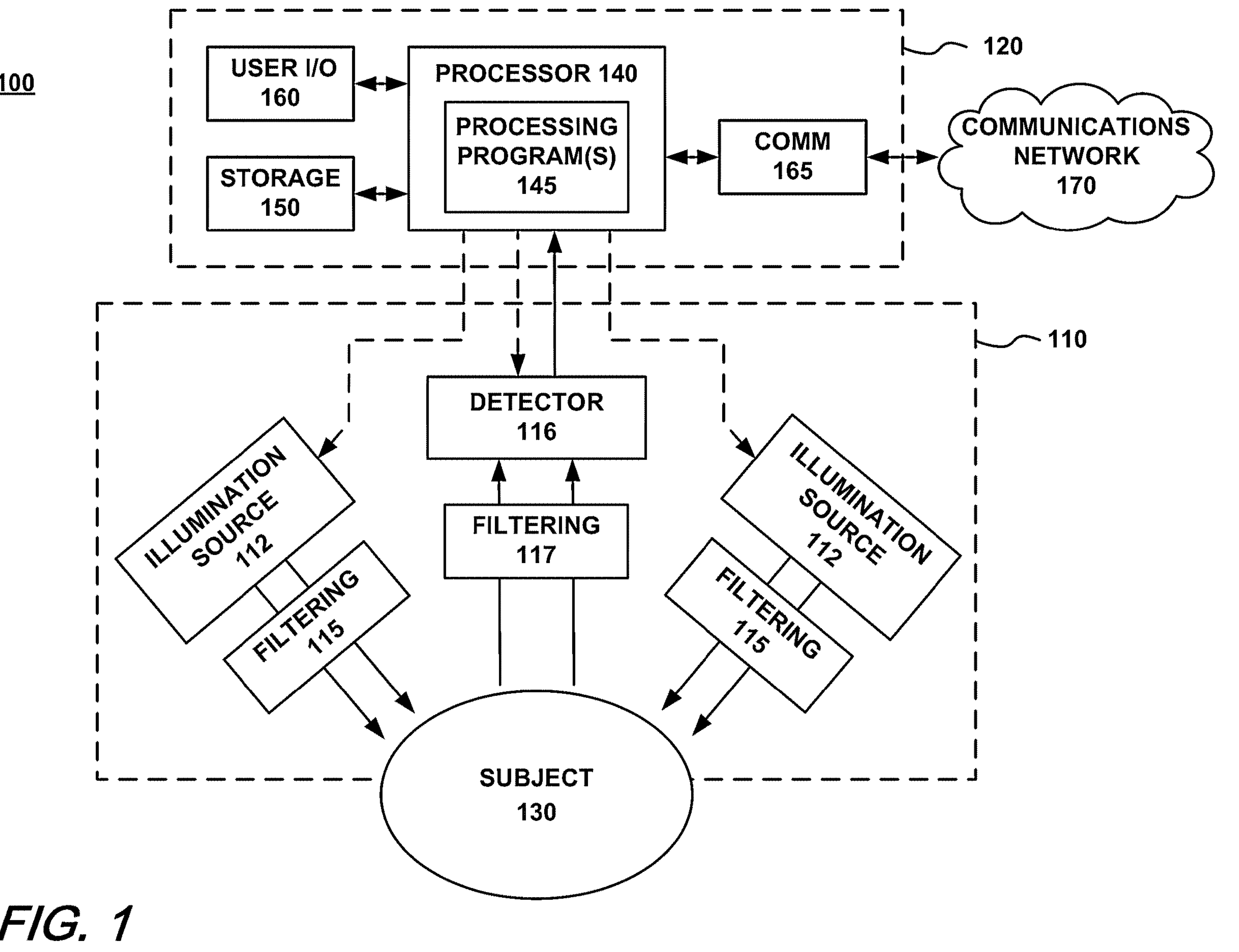
FIG. 1 is a schematic representation of an exemplary system in accordance with the present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, and the like represent various processes which may be substantially represented in computer readable medium and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flow chart elements or other elements indicating performance of process steps and/or textual description. Such modules may be executed by hardware that is expressly or implicitly shown.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture and a 3D volumetric image data might represent a stack of 2D images that represent a 3D volume of the object being imaged, such as a stack of MRI images. The term "image" as used herein may also refer to the results of processing one or more captured images to derive a further image.

FIG. 1 schematically depicts an exemplary system 100 in accordance with the present disclosure for grading the severity of acne in human skin. As shown in FIG. 1, components of system 100 include an image capture system 110 coupled with a processing system 120. Image capture system 110 may include one or more hand-held or mounted point-and-shoot or DSLR cameras, mobile cameras, frontal or rear-facing smart-device cameras, dermatoscopes (e.g., Canfield Scientific Inc.'s VEOS), 2D skin imaging systems (e.g., Canfield Scientific Inc.'s VISIA, VISIA-CR), 3D human body imaging devices (e.g., Canfield Scientific Inc.'s VECTRA), Canfield Scientific Inc.'s NEXA system, 3D Total Body systems (e.g., Canfield Scientific Inc.'s WB360), and/or 3D volumetric imaging devices like Canfield Scientific Inc.'s PRIMOS-CR, among others.

In exemplary embodiments, image capture system 110 includes one or more illumination sources 112 which are activated to shine light onto a subject's skin 130 through a respective filtering element 115. Light reflected or emitted from the subject tissue 130 is captured by a detector 116 through a filtering element 117. Each filtering element 115, 117 may include one or more filters for passing or blocking light of a selected wavelength or band of wavelengths, and/or polarizers, collectively "filters," which can be selectively placed in or out of the respective optical path of the filtering element. In exemplary embodiments, detector 116 may comprise a camera, such as a conventional digital SLR camera or the like, a digital video camera, or multiple one- or two-dimensional detectors, with similar or different characteristics. Multiple detectors 116 can be arranged to capture two- or three-dimensional images.

Advantageously, the captured images can be single mode or multimodal—including, for example, those from standard white light, polarized light, and/or fluorescent light—captured at selected wavelengths and/or illuminated with selected wavelengths of light. It should be noted that the term "light" as used herein is not necessarily limited to humanly visible electromagnetic radiation, and may include portions of the electromagnetic spectrum outside the visible range.

Images captured by image capture system 110 are provided to processing system 120 for processing as described below. Of further advantage, processing system 120 may also control image capture system 110, for example, by controlling one or more aspects of the image capture and/or illumination of the subject, such as exposure, modality, or filtering, among others.

Images may also be provided to processing system 120 from other sources and by other means. For example, images may be provided via communications network 170, or in a non-transitory, computer-readable storage medium, such as storage 150.

Processing system 120 includes a processor 140 that may be coupled to storage 150, for storing and retrieving images, among other data, and to input/output devices 160, such as a display device and/or user input devices, such as a keyboard, mouse, touchscreen, or the like. Processor 140 may also be coupled to a communications module 165 for interconnection with a communications network 170, such as the Internet, for transmitting and receiving images and/or data, and/or receiving commands, software updates or the like. Processing system 120 may be implemented, for example, with one or more central processing units, computers, workstations, PCs, tablet computers or the like, operating in accordance with one or more programs 145 embodied in a compatible, non-transitory, computer-readable storage medium. The interface between image capture system 110 and processing system 120 can be wired, wireless, direct, or indirect (e.g., via a network, Internet.)

It should be noted that the exemplary system 100 illustrates just one of a variety of possible arrangements contemplated by the present disclosure. For example, the various elements of system 100 need not be co-located. For example, image capture system 110 and I/O devices 160 can be located in a dermatologist's office and processor 140 and storage 150 can be remotely located, functioning within a tele-dermatology framework, or may be "cloud-based," interacting with image capture system 110 and I/O devices 160 over communications network 170. In other exemplary arrangements, I/O devices 160 can be remotely located from image capture system 110, thereby allowing a user to remotely examine subjects' images.

Figure 2:
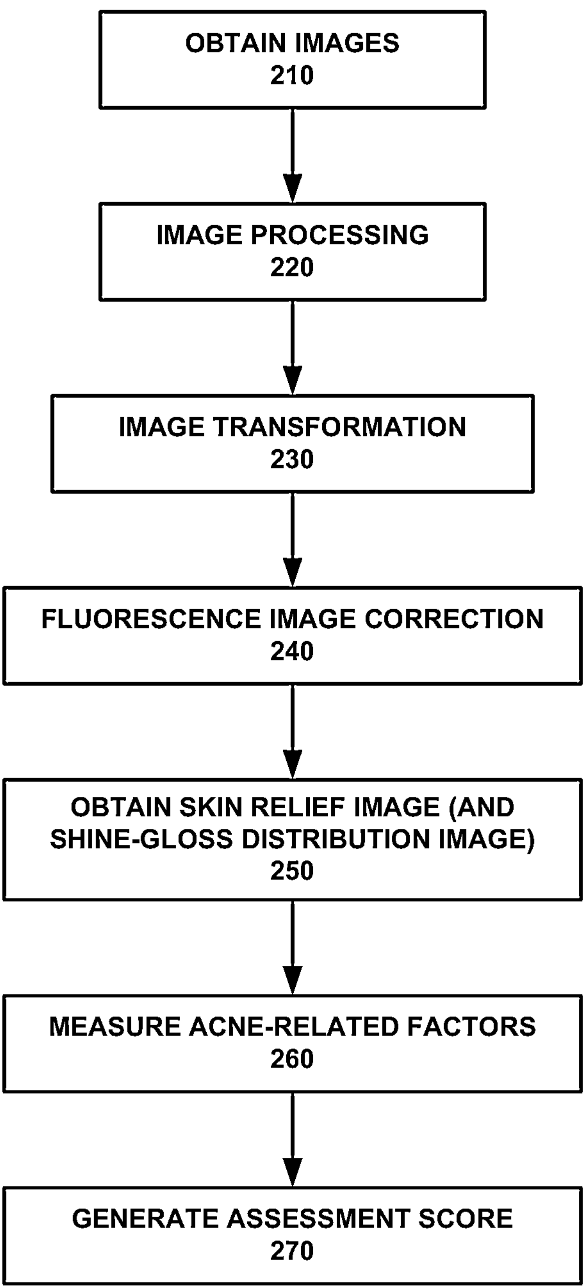
FIG. 2 is a flow chart depicting an exemplary method in accordance with the present disclosure.

FIG. 2 is a flowchart depicting an exemplary process 200, such as would be carried out with exemplary system 100 in accordance with the present disclosure. It is contemplated that in carrying out the exemplary image capture process, system 100 operates in accordance with program(s) 145 executed by processor 140.

As shown in FIG. 2, operation begins at 210 in which one or more images of a subject are obtained, such as, for example, by capture, input, reception, or reading from storage. In exemplary implementations, left, center and right, standard white light RGB, cross-polarized, parallel-polarized, fluorescence, and excitation absorption images of the subject's face are obtained at 210.

In exemplary implementations, the fluorescence images are images that have been captured with illumination and detection filtering selected so as to image the distribution of one or more porphyrins, such as coproporphyrin-III (CPIII) and/or protoporphyrin-IX (PPIX), which are characteristic of acne. A CPIII fluorescence image can be obtained, for example, by illuminating the subject skin with blue light of (e.g., of wavelength 400-410 nm), and capturing the image via green filtering (e.g., of a wavelength passband of 540-560 nm). Because PPIX fluorescence is at wavelengths greater than approximately 630 nm, a PPIX fluorescence image can be captured using a long-pass filter that allows wavelengths greater than 540 nm to pass and then separating the CPIII and PPIX fluorescence based on color, which can be obtained from an RGB image. Another method would be to capture the two fluorescence signals separately, with the PPIX fluorescence image being captured using a long-pass filter with wavelength 620-630 nm. Acne fluorescence imaging methods and apparatuses are described in U.S. Pat. No. 10,368,795, incorporated herein by reference in its entirety.

In addition to the aforementioned fluorescence images, corresponding excitation images are also preferably obtained at 210. Such an excitation image can be obtained by capturing an image of the skin illuminated with the same spectral band illumination used in capturing the corresponding fluorescence image, but with no filter in the detection path, or using a suitable neutral density filter to match the input light levels. The excitation images are used at 240, discussed further below, to normalize the corresponding fluorescence images for non-uniform light distribution, heterogeneous absorption of light due to tissue chromophores, filter leakage, and/or ambient light distribution.

Preferably, the set of images for each subject are captured in temporal proximity to each other, with the subject stationary so as to avoid or minimize the effects of any movement or changes in the subject's pose. Additionally, to maintain consistency between images, the same illumination source(s) are preferably used to the extent possible, such as by using the same broad-spectrum white light source and polarization as illumination when capturing parallel- and cross-polarized images of the same views, for example. Likewise, to the extent possible, the same sensor(s) are preferably used in capturing the images.

Figure 3A:
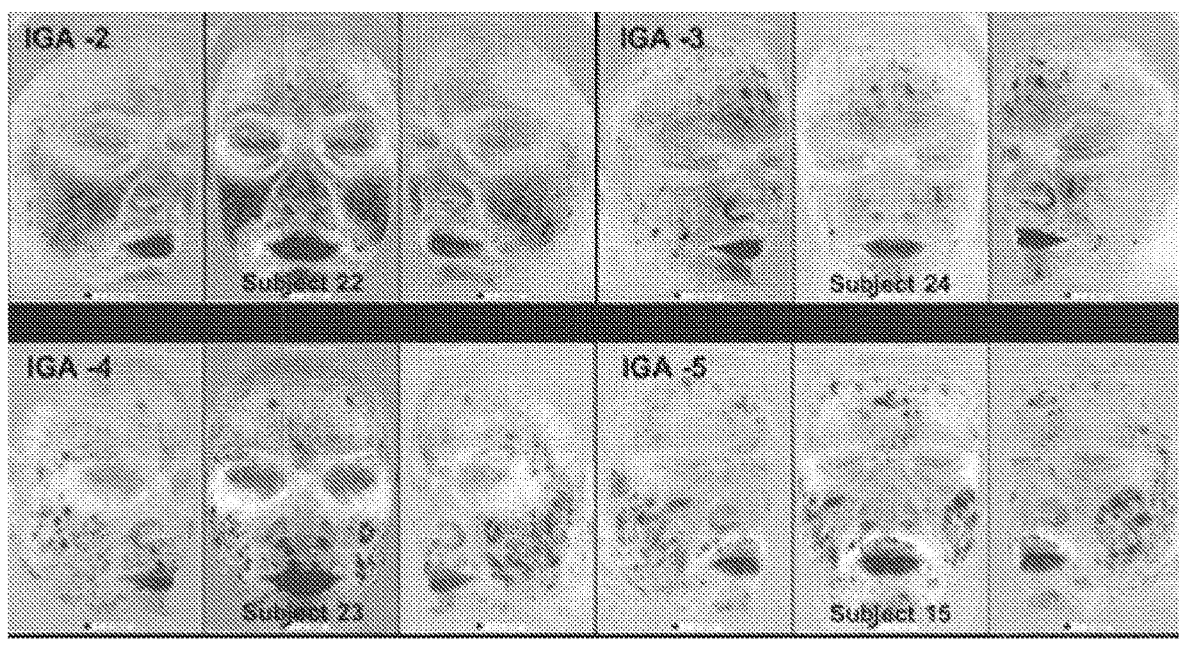
FIG. 3A shows illustrative RBX-Red images of four subjects of varying acne severity and FIG. 3B shows illustrative erythema detection images corresponding to the images of FIG. 3A, in accordance with the method of FIG. 2.
Figure 3B:
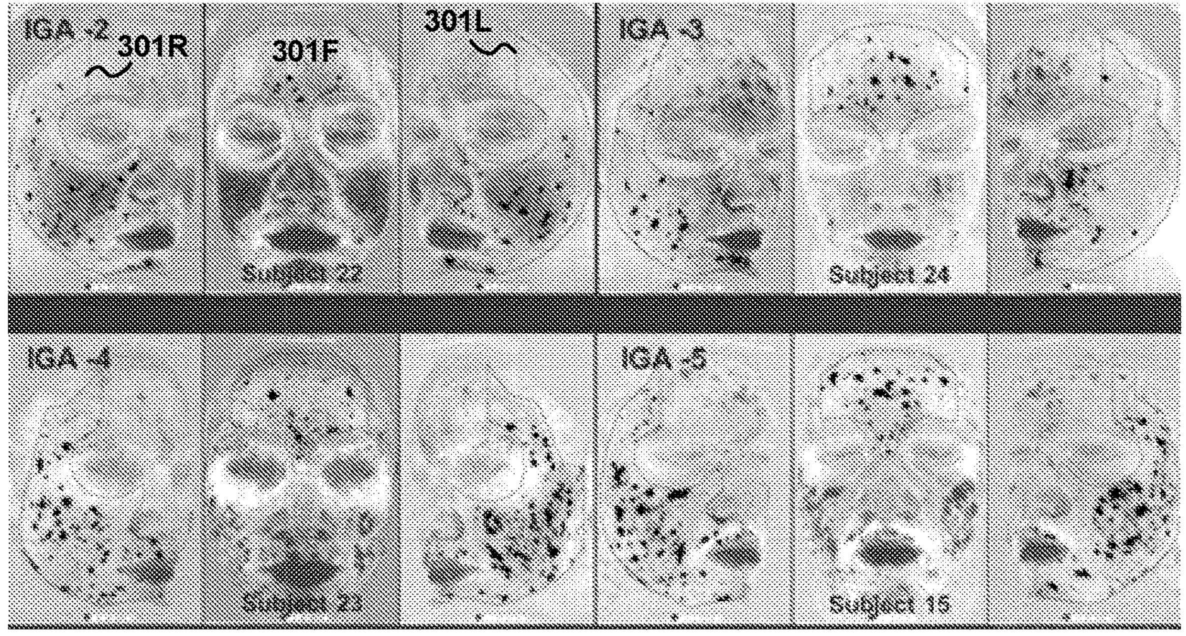

With the various images obtained at 210, operation then proceeds to 220, in which processing of the images is carried out. Such processing may include, for example, image registration, and defining areas of interest (AOIs) for analysis. As illustrated in FIG. 3B, two side-view AOIs 301L and 301R including the cheek and temple areas of the subject's face and a front view AOI 301F including the forehead and chin area, among other possibilities, can be delineated in exemplary implementations. The standard white light, polarized, and fluorescence images are elastically registered at 220 so that the same AOI would be used for analysis across imaging modalities.

Operation then proceeds to 230 in which image transformation and/or correction is performed to obtain one or more sets of derived images, including, for example, pigmentation (e.g., melanin, hemoglobin), texture, shine and/or surface oiliness images. In exemplary implementations, a Red/Brown/X (RBX) transformation is applied to the cross-polarized images to convert the RGB color data into Red and Brown images. RBX transformation uses a spectro-colorimetric model to extract hemoglobin (Red) and melanin (Brown) absorption and distribution information from cross-polarized images. RBX transformation methods and apparatuses are described in U.S. Pat. No. 8,498,460 and RE47,921, incorporated herein by reference in their entireties. FIG. 3A shows RBX-Red images of four subjects and the corresponding IGA grades assigned to them by investigators.

In exemplary implementations, instead of performing an RBX transformation at 230, the redness of erythema can be separated and measured by performing color analysis/color-space transformation of the standard or cross-polarized images.

Figure 4A:
FIG. 4A shows illustrative CPIII fluorescence images and FIG. 4B shows illustrative CPIII fluorescence detection images corresponding to the images of FIG. 3A, in accordance with the method of FIG. 2.

Operation then proceeds to 240 in which the fluorescence images are corrected, such as for pigment absorption of the excitation light using the corresponding excitation images obtained at 210. Suitable fluorescence imaging methods and apparatuses are described in U.S. Pat. No. 8,849,380, incorporated herein by reference in its entirety. FIG. 4A shows illustrative CPIII fluorescence images corresponding to the images of FIG. 3A.

Figure 5A:
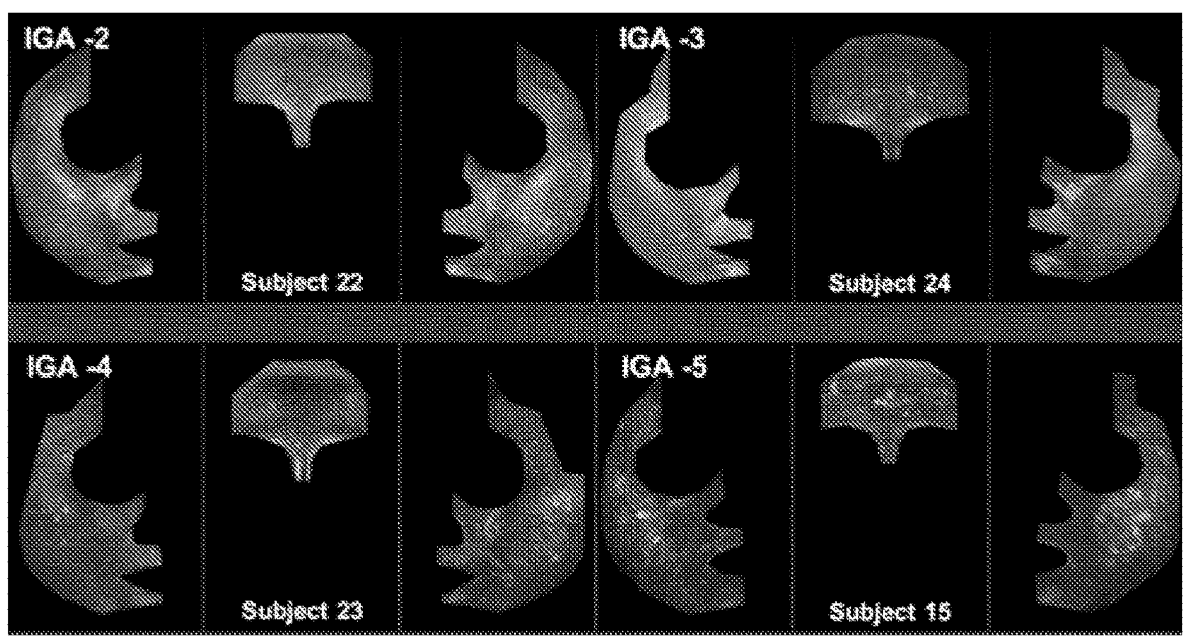
FIG. 5A shows illustrative skin texture images and FIG. 5B shows illustrative raised topography detection images corresponding to the images of FIG. 3A, in accordance with the method of FIG. 2.

Operation then proceeds to 250, in which a skin macro-micro relief image with textural features, and, optionally, a shine-gloss distribution map, are derived using the cross- and parallel-polarized images. The relief image can be generated using an image-fusion technique, such as described in U.S. Pat. No. 10,702,160, incorporated herein by reference in its entirety. It may also be possible to obtain the relief image by capturing actual three-dimensional data, such as with Canfield Scientific Inc.'s PRIMOS-CR system, for example. Skin surface oiliness and shine mapping and measurement methods and apparatuses are described in U.S. Patent Application Publication No. 2019/0336003A1, incorporated herein by reference in its entirety. FIG. 5A shows illustrative skin texture images corresponding to the images of FIG. 3A.

Operation then proceeds to 260, in which various acne-related factors are measured from the images as obtained and processed above. For each subject, the measurement of a factor can be made using each of the three views of the subject's face and combined to obtain a full-face measurement of that factor for the subject.

One such factor, acne-related erythema, or abnormal redness due to vasodilation, can be measured by analyzing the RBX-Red image to detect erythema within an AOI and determining the fractional area of erythema with respect to the AOI. As mentioned, FIG. 3A shows RBX-Red images of four subjects illustrating different levels of acne severity based on the IGA grade assigned to them. In FIG. 3B, the AOI in each view is shown by a blue border and the detected acne-related erythema is shown by black spots.

It should be noted that in FIGS. 3A-6 and associated description, an IGA grading scale of 0-5 is used, in which 0 represents no acne, 1 mild acne, 2 moderate acne, 3 advanced acne, 4 severe acne, and 5 very severe acne. As will be apparent, this particular IGA scale is merely illustrative and the principles described herein are not limited to any one particular acne severity grading scale, with other suitable grading scales being contemplated by the present disclosure.

In exemplary implementations, the detection of erythema, as illustrated in FIG. 3B, can be accomplished by applying an adaptive thresholding technique to the RBX-Red image, such as that shown in FIG. 3A. In such a technique, detection thresholds are set for each RBX-Red image of each subject. In each image, a normal level of redness within the respective AOI is estimated, and used to determine one or more threshold values for detecting areas within the AOI having higher level(s) of redness. Those areas that have levels of redness exceeding the threshold value(s) are treated as detected areas of erythema and their areas used to calculate the aforementioned fractional area of erythema within the AOI. Where multiple thresholds are used, the degree of redness of such areas can also be considered in calculating a metric indicative of acne-related erythema. For applications involving sequential images of a subject, threshold values determined for an earlier image can be applied in subsequent images. This allows measuring changes between sequential images, such as images taken before and after treatment, for example.

In exemplary implementations, erythema can be detected using artificial intelligence (AI) techniques. In such implementations, a neural network or other suitable AI arrangement that has been trained with images such as the RBX-Red images of FIG. 3A, is provided with RBX-Red images of particular subjects and detects areas of erythema, such as illustrated in the images of FIG. 3B. The AI arrangement can be implemented, for example, with one or more program(s) 145 executed by processor 140 of system 100, or can be remotely located and accessible to system 100 via communications network 170, among other possibilities.

It should be noted that for measuring acne-related inflammation, while a fractional area measurement can be used as described, some intensity measurement(s) such as mean and/or median intensity may be used as alternatives or in addition to the fractional area measurement.

Figure 4B:

Another factor that can be determined at 260 is the microbial activity of *C. acnes* bacteria or the comedonal feature of acne. This can be measured from the Coproporphyrin III (CPIII) fluorescence image, as obtained at 210 or as corrected at 240, in which the CPIII fluorescence emitted from within the pores is detected. FIG. 4A shows the as-captured CPIII fluorescence images for the same four subjects illustrated in FIGS. 3A and 3B. FIG. 4B shows images corresponding to those of FIG. 4A in which the fluorescence spots detected within the AOIs defined for each image are highlighted (in red). As mentioned, suitable fluorescence imaging techniques for this purpose are described in U.S. Pat. Nos. 8,849,380 and 10,368,795.

In exemplary implementations, fluorescence spots can be detected using AI techniques. In such implementations, a neural network or other suitable AI arrangement that has been trained with images such as the fluorescence images of FIG. 4A, is provided with fluorescence images of particular subjects and detects fluorescence spots, such as illustrated in the images of FIG. 4B. The AI arrangement can be implemented, for example, with one or more program(s) 145 executed by processor 140 of system 100 or can be remotely located and accessible to system 100 via communications network 170, among other possibilities.

It has been illustrated that the correlation between the CPIII fluorescence spots and comedones identified by physicians increases by measuring the sizes of only the most prominent spots. (See S. V. Patwardhan et al., Measuring acne using Coproporphyrin III, Protoporphyrin IX, and lesion-specific inflammation: an exploratory study, Arch. of Derm. Res., Apr; 309(3):159-167, 2017, DOI: 10.1007/s00403-017-1718-3.) Accordingly, in an exemplary implementation, the sizes of the detected fluorescence spots within an AOI of a subject can be measured and only those spots larger than some percentage (e.g., 20%) of the maximum spot size for that particular subject are kept. The total area of all such fluorescence spots larger than said percentage of the maximum spot size can be reported for the subject as a fractional area of the AOI.

Figure 5B:
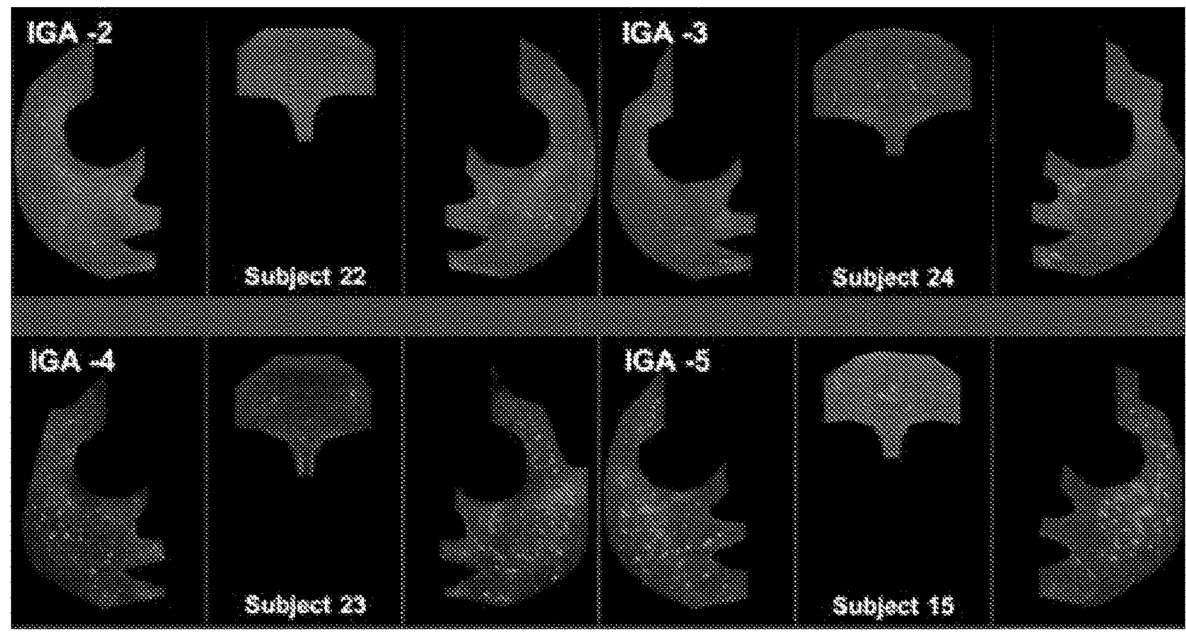

Another acne-related factor that can be determined at 260 is facial roughness associated with the raised topography of acne lesions. Facial roughness can be measured from the skin macro-micro relief texture image obtained at 250. The total raised area of all the acne lesions within an AOI on a subject's face can be detected and reported as a fractional area of the AOI. FIG. 5A shows illustrative relief texture images corresponding to the images of FIG. 3A. FIG. 5B shows corresponding raised topography detection images in which the raised lesion areas in the texture images of FIG. 5A are highlighted (in red).

In the relief texture images such as shown in FIG. 5A, the skin surface depth or height is translated into a gray scale, with deeper features (such as wrinkles and pores) shown as darker areas and raised features (such as lesions) shown as brighter areas. In exemplary implementations, to generate the corresponding raised topography detection images such as shown in FIG. 5B, lighter areas in the relief texture images that are generally circular and have brighter centers (like a mountain with its bright peak encircled by a progressively darker perimeter representing lower heights) are detected and highlighted, such as illustrated by the red areas in the images of FIG. 5B. Such detection can be done, for example, using suitable brightness and shape filtering techniques. It should be noted, however, that some raised lesions may not have circular distributions due to shadows in the parallel-polarized image from which the relief texture image was derived. Such shadows depend largely on the location of the lesion and the angles of illumination and/or capture. Such issues can be avoided, for example, by using true 3D imaging data, such as can be provided with a PRIMOS-CR system, or the like. Moreover, with 3D data, true surface-area and/or volume measurements can be used instead of or in addition to the fractional raised area as acne severity metric(s). As such, using 3D images of the skin, the surface area of the raised skin portions due to acne can be measured. Additionally or alternatively, the volume of the raised skin portions due to acne can be measured as well.

In exemplary implementations, raised areas can be detected using AI techniques. In such implementations, a neural network or other suitable AI arrangement that has been trained with images such as the relief texture images of FIG. 5A, is provided with relief texture images of particular subjects and detects raised areas, such as illustrated in the images of FIG. 5B. The AI arrangement can be implemented, for example, with one or more program(s) 145 executed by processor 140 of system 100 or can be remotely located and accessible to system 100 via communications network 170, among other possibilities.

Additionally at 260, the fractional area of skin surface oiliness and shine can be measured from the combination of cross- and parallel-polarize images. (See, e.g., U.S. Patent Application Publication No. 2019/0336003A1.) It has been shown that these two measurements are complementary to each other and strongly correlate with both the amount of skin surface oil and the clinical evaluation of the subject's face for oiliness. (I. Kohli et al., Quantitative measurement of skin surface oiliness and shine using differential polarized images, Arch. of Derm. Res., 2020. DOI: 10.1007/s00403-020-02070-5.)

The various images can also be analyzed for detecting inflammatory and non-inflammatory acne lesions. The lesions identified from image analysis can be compared with those identified by the investigators. Comparisons can include total lesion counts, and/or locations on the subject's face, for example. For example, some IGA grading schemes include as a factor the location(s) and numbers of lesions on the face; e.g., whether there are lesions on the entire face, only half of the face, just on the cheeks or forehead, etc. Accordingly, lesion counts and/or locations can be determined at 260 and incorporated into an acne assessment grade, such as described below.

Operation then proceeds to 270 in which an assessment grade, referred to herein as a Parametric Acne Severity (PAS) Score, is generated for each subject using some or all of the measurements determined at 260. In exemplary implementations, the aforementioned measurements are normalized with respect to their expected maximum values and an equally weighted linear combination of the normalized measurements is used to generate the PAS score for each subject. In exemplary implementations, for example, the fractional areas (relative to AOI) of erythema, raised lesions, and fluorescence spots (larger than a certain size), determined as described above, are linearly combined to generate the PAS score. Moreover, as discussed above, instead of or in addition to using the fractional area of raised lesions, actual surface area and/or volumetric measurements can be used where 3D imaging data has been obtained.

In exemplary implementations, the PAS Score can be generated using AI techniques. In such implementations, a neural network or other suitable AI arrangement that has been trained with sets or subsets of images such as those described herein, is provided with images of particular subjects and based thereon generates an acne severity score, such as the PAS Score described herein. In exemplary implementations, a combination of the standard, polarized, and/or fluorescence images, without additional, derived images, such as the RBX-Red and texture images, can be used as training and inputs for the AI arrangement. In further exemplary implementations, derived images such as the RBX-Red and/or texture images may also be used. The AI arrangement can be implemented, for example, with one or more program(s) 145 executed by processor 140 of system 100 or can be remotely located and accessible to system 100 via communications network 170, among other possibilities.

Once determined as described, the PAS score, or an alphanumeric, graphical, visual or other suitable representation thereof, can then be displayed, stored, communicated, or further processed.

Testing and Results 24 mild to severe acne subjects were examined independently by two investigators. Ten subjects were of skin type I, six were of skin type II, none were of skin type III, four were of skin type IV, two were of skin type V, and two were of skin type VI.

Acne inflammatory and non-inflammatory lesions were counted and an IGA severity grade in a range of 1 to 5 was given to each subject by each investigator. Before each subject's assessment, multi-modality facial images of the subject were captured using Canfield Scientific Inc.'s VISIA-CR imaging system. The facial images captured were such as those described above, including standard white, parallel- and cross-polarized, and fluorescence images. The system was configured to display the subject's as-captured side and front views to an investigator during live examination of the subject. When identifying and counting the lesions on the subject's face, each investigator marked the locations of the lesions on the displayed clinical images. The lesions marked by both investigators were then overlaid in two colors on the subject's clinical images and presented to the investigators together for consensus along with each investigator's IGA grade. The investigators then reexamined the subject for lesions that were not mutually identified and decided whether to keep these lesions.

The aforementioned multi-modal images of the subjects were then provided to an exemplary system as described herein. The various acne-related feature measurements described above were determined individually and each compared with the IGA grades assigned by the investigators to the same set of subjects. A subset of these measurements were then used to generate a Parametric Acne Severity (PAS) Score for each subject, as described above. For the implementation used in this testing procedure, the shine/skin surface oiliness measurements of the subjects were not considered in generating the PAS scores. The PAS scores thus determined were then compared to the IGA grades.

There was a strong agreement between the inflammatory and non-inflammatory lesions identified from the images and those identified by the investigators. The correlation coefficients when compared per view for the inflammatory and non-inflammatory lesion counts were 0.77 and 0.85, respectively. When the lesion counts were compared with the IGA grades, no relationship was identified between the two. The correlation coefficients between inflammatory and non-inflammatory lesion counts and IGA grades were 0.47 and 0.08, respectively.

Figure 6:
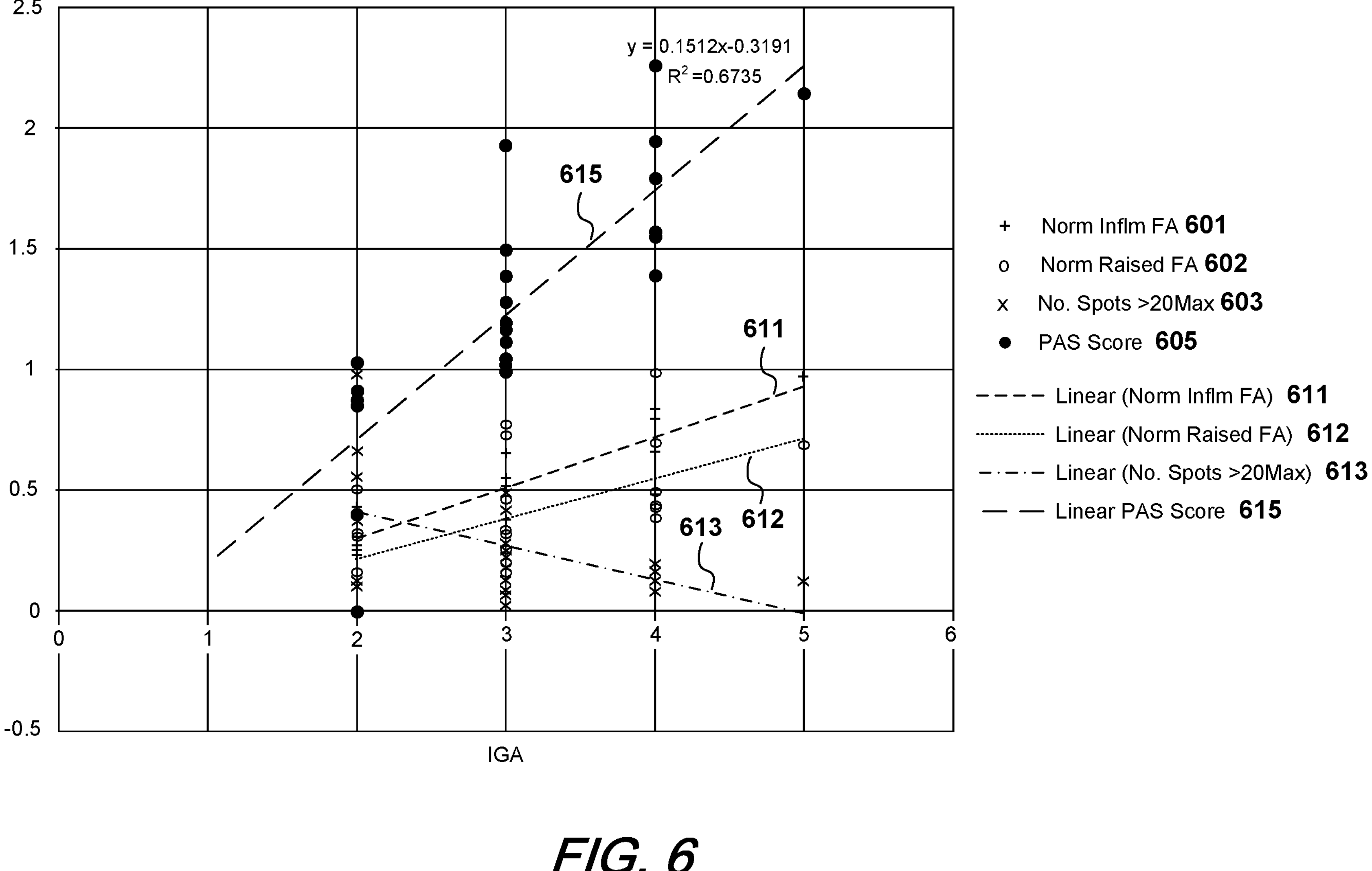
FIG. 6 is a graph showing the relationships between various acne-related factors and IGA and of a combination of such factors and IGA.

FIG. 6 shows a scatter plot of the individual acne feature measurements (represented as 601-603) used in this implementation with respect to the corresponding IGA grades assigned to the subjects. This scatter plot also includes the PAS scores 605, calculated as the linear combination of the measurements 601-603. FIG. 6 also shows a linear regression line 615 for the PAS scores 605 and a line 611-613 for each of the constituent measurements 601-603, respectively. The measurements shown in FIG. 6 are normalized measurements.

The acne inflammation measurement 601 (line 611) showed the strongest relationship to IGA, with a correlation coefficient of 0.85 ($p<0.01$), followed by acne lesions raised texture 602 (line 612), with a correlation coefficient of 0.6 ($p<0.01$). An inverse relationship was observed between the measurement 603 (line 613) of prominent CPIII fluorescence spots (i.e., those spots larger than 20% of the largest spot for that subject) and IGA grades, with a correlation coefficient of 0.51 ($p<0.01$). The correlation coefficient between the PAS score 605 (line 615) and the IGA grades was 0.82 ($p<0.05$).

No relationship was observed between shine/skin surface oiliness and the IGA grades, with a correlation coefficient of 0.044 ($p<0.01$). Said measurements were not included in the determination of the PAS score 605 and are not represented in FIG. 6.

Aside from visual clues, a practitioner will also typically palpate a subject's skin to identify and confirm acne lesions. According to FDA guidelines, however, an IGA grade is to be given by evaluating the subject from at least three feet away. It is difficult to see and identify comedones and small inflammatory lesions when standing away from the subject. Although most of the IGA grading scales describe the number of acne lesions (using terms such as "none", "few", "moderate", and "many"), there is no clear relationship between the actual lesion counts and the IGA grades.

When a subject is evaluated for acne severity from a distance of three or more feet, two features are most evident: erythema (redness) and raised skin topography or skin roughness. Because of this, it is understandable that the measurements of these two factors correlate well with IGA. A subject's acne scars and post-acne hyperpigmentation are not evaluated when judging severity and assigning an IGA grade to the subject. Typically, subjects with acne scars and hyperpigmentation are excluded from acne treatment studies. If these factors need to be included in an acne severity assessment, however, then roughness due to scars can be included in the texture measurement and hyperpigmentation can be measured from the RBX-Brown images. A suitable pigmentation measurement technique that can be used in exemplary implementations is described in G. Dobos et al., Effects of intrinsic aging and photodamage on skin dyspigmentation: an explorative study, J. Biomed Opt., 2016 Jun. 1; 21 (6): 66016. DOI: 10.1117/1.JBO.21.6.066016. PMID: 27330007. 3D images captured using Canfield Scientific Inc.'s PRIMOS fringe-projection, or VECTRA Stereo-photogrammetric techniques can also be used for skin topography/roughness measurements. Also, instead of RBX-Brown images, hyperpigmentation can be measured from absorption imaging using wavelengths in the UV-NIR spectral band. Canfield Scientific Inc.'s VISIA-CR system, for example, can be used for this purpose.

How well an evaluator is able to identify comedones while standing three feet away from the subject is questionable. The measurements of prominent CPIII fluorescence spots, however, seem to be related to IGA. When excited with illumination of a 400-410 nm wavelength, peak CPIII fluorescence is within a band of wavelengths of 570-610 nm. The characteristic oxy-deoxy-hemoglobin absorption peaks are also within the same spectral band. It should be noted that fluorescence from CPIII in an erythematic neighborhood will be absorbed by the hemoglobin and will not be detected by the camera. Since higher IGA grades correspond to more severe acne and thus more erythema, more of the fluorescence emitted from the CPIII characteristic of acne is absorbed and thus less of this fluorescence is detected. This supports the inverse relationship between acne severity/IGA grade and the CPIII fluorescence measurements 603. It should be noted that if the captured fluorescence image is corrected for the absorption of the emitted fluorescence, a direct relationship between the fluorescence image thus corrected and acne severity score would apply. In either case, whether the relationship is direct or inverse, good correlation with acne severity allows the detected fluorescence to be used in generating a severity score.

Additionally, visually evaluating skin surface oiliness is highly dependent on ambient lighting and its direction on the subject's face. Moreover, skin surface oiliness is judged by evaluators mostly based on shine. Although over-stimulated sebaceous glands producing excess amounts of sebum is a contributing factor for acne, skin surface oil is not included in the IGA evaluation. For consistency with IGA, therefore, skin surface oiliness can be excluded from the PAS score in exemplary implementations, such as described above. This does not, however, preclude the use of skin surface oiliness in the determination of other scores.

While the use in implementations as described above of an equally weighted linear combination of multi-factorial measurements provides good agreement with IGA, other combinations of the factors described may be possible, given more data and testing. Also, other factors not described herein, measurements from non-imaging methods, and subject-specific inputs and data can be included in the assessment model.

With large numbers of images and data, machine learning/deep learning/artificial intelligence techniques can be used in exemplary implementations to generate the acne severity score. Advantageously, the multi-factorial approach described herein will provide additional insights about the acne and suitable treatments than could be achieved with just a resultant numerical grade. Besides providing a global assessment measurement, implementations in accordance with the present disclosure can also provide measurements of individual factors contributing to acne severity and changes in those factors due to treatment or course. In addition, analyzed images can be presented and evaluated along with the measurements by the evaluator for confirmation.

Implementations as described herein can provide acne assessment scoring which can be used as an objective measure of acne severity and which can be used to determine changes in acne severity, such as due to treatment or disease course. Such scoring can bring standardization to acne assessment in clinical trials, provide more sensitive measurements for studying treatment effects, and allow clinicians to confidently observe the relative effectiveness of different types of treatment, among other benefits. In addition to measuring and evaluating treatment efficacy using before and after images and/or measurements, implementations in accordance with the present disclosure can also be used in measurement-based treatment and/or making treatment suggestions, among other applications.

The foregoing merely illustrates principles of the present disclosure and it will thus be appreciated that those skilled in the art will be able to devise numerous alternative arrangements which, although not explicitly described herein, embody the principles of the present disclosure and are within its spirit and scope. For instance, as can be appreciated, a variety of arrangements of processing and imaging systems and devices are contemplated consistent with the present disclosure. Additionally, although illustrated as single elements, each block or step shown may be implemented with multiple blocks or steps, or various combinations thereof. Also terms such as "software," "application," "program," "firmware," or the like, are intended to refer, without limitation, to any instruction or set of instructions, structure, or logic embodied in any suitable, non-transitory, machine-readable medium. It is to be understood that numerous modifications may be made to the illustrative embodiments and that other arrangements may be devised without departing from the spirit and scope of the present invention as defined by the appended claims.

What is claimed is:

1. A method comprising:

obtaining a cross-polarized image with a skin area appearing therein;

transforming the cross-polarized image to generate a red component image;

detecting erythema in the skin area using the red component image;

obtaining a texture image with the skin area appearing therein;

detecting raised portions of the skin area using the texture image;

generating an acne severity score based on the erythema and raised portions detected in the skin area; and outputting an indication of the acne severity score.

2. The method of claim 1 comprising:

obtaining a fluorescence image with the skin area appearing therein; and detecting portions of the skin area containing a porphyrin indicative of acne, wherein the acne severity score is generated based on said detected portions of the skin area.

3. The method of claim 2 comprising performing one or more correction operations on at least one of the parallel-polarized image, the cross-polarized image, or the fluorescence image.

4. The method of claim 2 comprising:

obtaining an excitation image with the skin area appearing therein;

correcting the fluorescence image using the excitation image; and using the corrected fluorescence image to detect the portions of the skin area containing the porphyrin.

5. The method of claim 2, wherein generating the acne severity score includes:

determining a first metric based on the erythema detected in the skin area;

determining a second metric based on the raised portions detected in the skin area;

determining a third metric based on the detected portions of the skin area containing the porphyrin; and calculating a combination of the first, second and third metrics.

6. The method of claim 1 comprising obtaining a parallel-polarized image with the skin area appearing therein, wherein the texture image is generated using a combination of the parallel- and cross-polarized images.

7. The method of claim 1, wherein detecting erythema in the skin area includes applying an adaptive thresholding technique to the red component image.

8. The method of claim 1, wherein detecting raised portions of the skin area includes identifying in the texture image generally circular areas with centers brighter than their perimeters, including applying at least one of a brightness or a shape filtering operation to the texture image.

9. The method of claim 1, wherein transforming the cross-polarized image to generate a red component image includes performing an RBX transformation of the cross-polarized image.

10. The method of claim 1, wherein:

the texture image is a three-dimensional image with the skin area appearing therein; and the method includes using the texture image to measure at least one of the surface area or the volume of the raised portions of the skin area.

11. A non-transitory computer readable storage medium containing instructions for execution by a processor for carrying out the method of claim 1.

12. An apparatus comprising:

a storage device configured to store instructions; and a processor configured to execute instructions stored in the storage device to:

obtain a cross-polarized image with a skin area appearing therein;

transform the cross-polarized image to generate a red component image;

detect erythema in the skin area using the red component image;

obtain a texture image with the skin area appearing therein;

detect raised portions of the skin area using the texture image;

generate an acne severity score based on the erythema and raised portions detected in the skin area; and output an indication of the acne severity score.

13. The apparatus of claim 12, wherein the processor is configured to execute instructions to:

obtain a fluorescence image with the skin area appearing therein; and detect portions of the skin area containing a porphyrin indicative of acne, wherein the acne severity score is generated based on said detected portions of the skin area.

14. The apparatus of claim 13, wherein the processor is configured to execute instructions to perform one or more correction operations on at least one of the parallel-polarized image, the cross-polarized image, or the fluorescence image.

15. The apparatus of claim 13, wherein the processor is configured to execute instructions to:

obtain an excitation image with the skin area appearing therein;

correct the fluorescence image using the excitation image; and use the corrected fluorescence image to detect the portions of the skin area containing the porphyrin.

16. The apparatus of claim 13, wherein the processor is configured to execute instructions to generate the acne severity score by:

determining a first metric based on the erythema detected in the skin area;

determining a second metric based on the raised portions detected in the skin area;

determining a third metric based on the detected portions of the skin area containing the porphyrin; and calculating a combination of the first, second and third metrics.

17. The apparatus of claim 12, wherein the processor is configured to execute instructions to:

obtain a parallel-polarized image with the skin area appearing therein, and generate the texture image using a combination of the parallel- and cross-polarized images.

18. The apparatus of claim 12, wherein the processor is configured to execute instructions to detect erythema in the skin area by applying an adaptive thresholding technique to the red component image.

19. The apparatus of claim 12, wherein the processor is configured to execute instructions to detect raised portions of the skin area including identifying in the texture image generally circular areas with centers brighter than their perimeters, including applying at least one of a brightness or a shape filtering operation to the texture image.

20. The apparatus of claim 12, wherein the processor is configured to execute instructions to transform the cross-polarized image to generate a red component image by performing an RBX transformation of the cross-polarized image.

21. The apparatus of claim 12, wherein:

the texture image is a three-dimensional image with the skin area appearing therein; and the processor is configured to execute instructions to use the texture image to measure at least one of the surface area or the volume of the raised portions of the skin area.

* * * * *